(12) United States Patent
LoPesio et al.

(10) Patent No.: US 10,182,573 B2
(45) Date of Patent: Jan. 22, 2019

(54) ANTIMICROBIAL SOLUTION FOR USE WITH DENTAL APPLIANCES

(71) Applicant: FRESHGUARD DEFENSE LLC, Long Lake, MN (US)

(72) Inventors: Patricia M. LoPesio, Long Lake, MN (US); Lisa A. Zuraw, Charleston, SC (US)

( * ) Notice: Subject to any disclaimer, the term of this patent is extended or adjusted under 35 U.S.C. 154(b) by 912 days.

(21) Appl. No.: 14/289,854

(22) Filed: May 29, 2014

(65) Prior Publication Data
US 2014/0271948 A1 Sep. 18, 2014

Related U.S. Application Data

(63) Continuation-in-part of application No. 12/931,936, filed on Feb. 15, 2011.

(51) Int. Cl.
*A01N 65/36* (2009.01)
*A01N 65/00* (2009.01)
*A01N 37/02* (2006.01)

(52) U.S. Cl.
CPC ........... *A01N 65/36* (2013.01); *A01N 37/02* (2013.01); *A01N 65/00* (2013.01)

(58) Field of Classification Search
None
See application file for complete search history.

(56) References Cited

U.S. PATENT DOCUMENTS

| 4,941,995 A * | 7/1990 | Richards | D06M 16/00 252/407 |
| 6,706,256 B2 * | 3/2004 | Lawlor | A23G 3/36 424/440 |
| 2002/0068039 A1 * | 6/2002 | Pan | A61K 8/21 424/52 |
| 2003/0099603 A1 * | 5/2003 | Rajaiah | A61K 8/02 424/53 |
| 2006/0198797 A1 * | 9/2006 | Giniger | A61K 8/03 424/53 |
| 2009/0038624 A1 * | 2/2009 | Akervall | A63B 71/085 128/861 |
| 2009/0162483 A1 * | 6/2009 | Constantine | A23L 2/52 426/62 |
| 2009/0175806 A1 * | 7/2009 | Modak | A61K 8/365 424/58 |
| 2013/0323388 A1 * | 12/2013 | Talsma | A61K 8/34 426/533 |

FOREIGN PATENT DOCUMENTS

| GB | 2297557 A | * 8/1996 | ............ C11B 9/02 |
| WO | WO-00/11956 | * 3/2000 | ............ A01N 63/02 |

OTHER PUBLICATIONS

Science Daily (Academy of General Dentistry. "To Keep Mouths Safe, Don't Just Wear a Mouthguard; Keep It Clean." Dec. 12, 2007).*
Cvetnic et al. (Acta Pharm 54 (2004) 243-250) (Year: 2004).*

* cited by examiner

*Primary Examiner* — Abigail Vanhorn
*Assistant Examiner* — Jessica Kassa
(74) *Attorney, Agent, or Firm* — Cardle Patent Law Chtd

(57) ABSTRACT

In various aspects, the composition of matter disclosed herein includes an antimicrobial solution. The antimicrobial solution may include deionized water QS, acetic acid, and grapefruit seed extract (GSE) in combination with one another. The GSE may be at a concentration effective to eradicate microorganisms, and the microorganisms may include both Gram-positive microorganisms and Gram-negative microorganisms. This Abstract is presented to meet requirements of 37 C.F.R. § 1.72(b) only. This Abstract is not intended to identify key elements of the apparatus and methods disclosed herein or to delineate the scope thereof.

12 Claims, 8 Drawing Sheets

ANTIMICROBIAL SOLUTION FOR USE WITH DENTAL APPLIANCES

CROSS-REFERENCE TO RELATED APPLICATIONS

The present application is a continuation-in-part of application Ser. No. 12/931,936 filed on 15 Feb. 2011 and entitled MULTI-PURPOSE DENTAL APPLIANCE CLEANER, which is hereby incorporated by reference in its entirety herein.

BACKGROUND OF THE INVENTION

Field

This disclosure relates to dental appliances, and, more specifically, to an antimicrobial solution that may eradicate microorganisms growing on such dental appliances.

Background of the Related Art

Microorganisms may grow upon the surface of a dental appliance and inside pores in the materials of which the dental appliance is comprised. These microorganisms may cause malodor and may pose a health hazard to the user. For example, microorganisms found upon a dental appliance may include disease-causing organisms such as *Staphylococcus, Streptococcus,* and *Pneumococcus.* Pore may include, for example, pores, cracks, crevices, cavities, scratches, and surface imperfections. The dental appliance may include a metal portion and a plastic portion, and pores may be found in the metal portion, in the plastic portion, or both the metal portion and the plastic portion.

Unless the user cleans the dental appliance to remove the microorganisms, the microorganisms on the dental appliance may cause gum infections and tooth decay. The microorganisms may travel from the dental appliance to the lungs to produce exercise-induced asthma and other illnesses. Microorganisms reaching the stomach from the dental appliance may produce toxins causing nausea, vomiting and diarrhea. Moreover, if the user has cuts or irritation of the tissue of the mouth, microorganisms such as *Staphylococcus aureus* may enter the bloodstream during use of the dental appliance. In extreme cases, diseases resulting from microorganisms on the dental appliance may be fatal.

In a personal case involving the son of one of the inventors, the combination of a broken tooth and a dirty dental appliance (a mouth guard) resulted in a severe staph infection that ate away at the bone and cartilage in the base of his nose. Treatment included three surgeries and resulted in the missing of two months of school and three-plus months of the athletic season. This case is indicative of the danger associated with a dirty dental appliance, and motivated the search for an appropriate cleaner for dental appliances.

Methods known for cleaning a dental appliance include rinsing with water, soap and water, toothpaste, or denture cleaners. These methods may leave at least 10% of the microorganisms on the dental appliance. Such approaches may be ineffective in removing microorganisms trapped inside pores of the dental appliances, and may not remove foreign matter including embedded odors from the dental appliance.

Many products for cleaning dental appliances may contain components like zinc, Triclostan, bleaching agents, persulfate, monopersulfate, and ethylenediaminetraacetic acid ("EDTA"), which is a metal ion chelating agent and blood thinner. Such components may cause allergic reactions, and even more severe injuries like permanent neurological nerve damage to the user if ingested. Such allergic reactions may include tissue damage; rashes, hives, and irritations; gum tenderness; breathing problems; kidney failure; and low blood pressure. These serious incidents arising from the use of such products have caused the U.S. Food and Drug Administration ("FDA") to issue a public health alert in 2008, and require a health warning on the product packaging.

There may be 40 million mouth guard users in the U.S. Perhaps 35 million people have been diagnosed with TMJ, and the primary treatment is the use of a splint (night guard). A growing population has sleep apnea, which may require the use of a cpap machine and associated mouth appliance. Additionally, each year 4 million people may be fitted with braces in the U.S. All of these dental appliances are carriers of dangerous germs, bacteria, molds, and, worse yet, may smell awful.

Accordingly, there is a need for improved compositions of matter for the cleaning of a dental appliance.

BRIEF SUMMARY OF THE INVENTION

These and other needs and disadvantages may be overcome by the composition of matter disclosed herein. Additional improvements and advantages may be recognized by those of ordinary skill in the art upon study of the present disclosure.

In various aspects, the composition of matter disclosed herein includes an antimicrobial solution. The antimicrobial solution may include deionized water QS, acetic acid, and grapefruit seed extract (GSE) in combination with one another. The GSE may be at a concentration in the antimicrobial solution effective to eradicate microorganisms. Microorganisms eradicated by GSE may include both Gram-positive microorganisms and Gram-negative microorganisms.

In various aspects, the antimicrobial solution excludes multi-valent metal cations, metal cations other than alkali metal cations, allergy-inducing agents, anti-calculus agents, anti-plaque agents, fluoride ion source, desensitizing agents, H2 antagonists, or chemically-derived malodor control agents.

The composition of matter disclosed herein may include, in various aspects, pores formed in a surface of a dental appliance with microorganisms resident within the pores, and the surface including the microorganisms resident within the pores may be in contact with the antimicrobial solution. The dental appliance may be formed as a mouth guard.

This summary is presented to provide a basic understanding of some aspects of the apparatus and methods disclosed herein as a prelude to the detailed description that follows below. Accordingly, this summary is not intended to identify key elements of the apparatus and methods disclosed herein or to delineate the scope thereof.

Figure 1:
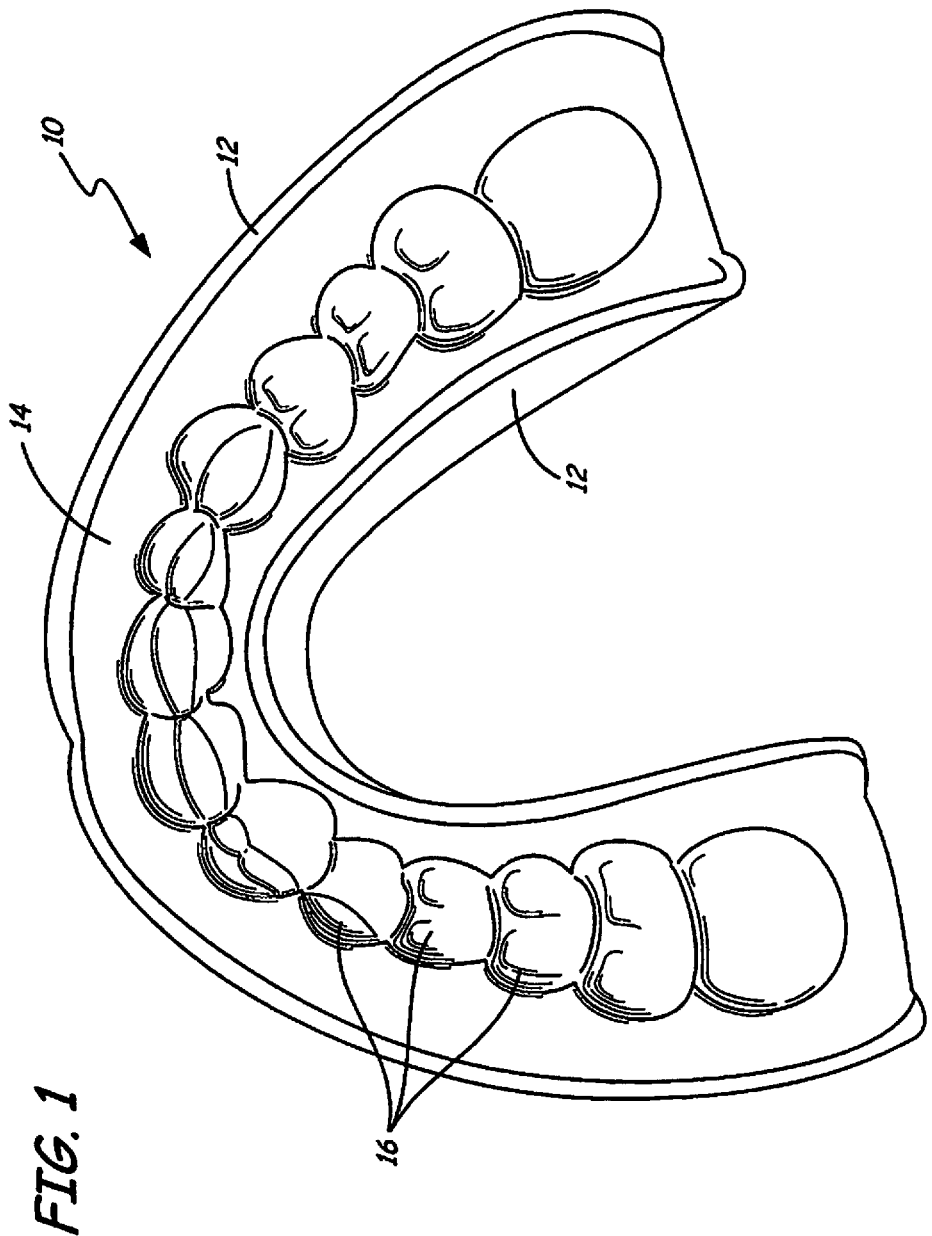
FIG. 1 illustrates by a perspective view portions of an exemplary dental appliance.

The Figures are exemplary only, and the implementations illustrated therein are selected to facilitate explanation. The number, position, relationship and dimensions of the elements shown in the Figures to form the various implementations described herein, as well as dimensions and dimensional proportions to conform to specific force, weight, strength, flow, composition, and similar requirements are explained herein or are understandable to a person of ordinary skill in the art upon study of this disclosure. Where used in the various Figures, the same numerals designate the same or similar elements. Furthermore, when the terms "top," "bottom," "right," "left," "forward," "rear," "first," "second," "inside," "outside," and similar terms are used, the terms should be understood in reference to the orientation of the implementations shown in the drawings and are utilized to facilitate description thereof. Use herein of relative terms such as generally, about, approximately, essentially, may be indicative of engineering, manufacturing, or scientific tolerances such as ±0.1%, ±1%, ±2.5%, ±5%, or other such tolerances, as would be recognized by those of ordinary skill in the art upon study of this disclosure.

DETAILED DESCRIPTION

A composition of matter is disclosed herein. In various aspects, the composition of matter includes a dental appliance, and the dental appliance may be formed of metal, plastic, or combinations of metal and plastic. The metal or plastic may be porous, and microorganisms may be resident within the pores. The composition of matter may include an antimicrobial solution that may be in contact with the dental appliance including microorganisms resident within the pores. In various aspects, the antimicrobial solution includes acetic acid, and the solution further includes a plant-based antimicrobial extract at a concentration effective to eradicate the microorganisms. The antimicrobial solution may be devoid of metal cation-based antimicrobial agents, in various aspects. In various aspects, the antimicrobial solution may take the form of a rinse that eradicates microorganisms from the dental appliance immersed therein. The antimicrobial solution may be incorporated into a towelette that may be applied to the dental appliance including porous plastic material portions thereof in order to eradicate microorganisms resident upon the dental appliance, in some aspects. The antimicrobial solution may be effective to eradicate both various Gram-negative and various Gram-positive bacteria.

The antimicrobial solution disclosed herein, in various aspects, contains only natural ingredients for eradicating microorganisms from the dental appliance and removing foreign material from the dental appliance. The antimicrobial solution disclosed herein, in various aspects, does not include chemicals that might degrade or harden the plastic or metal materials used in the dental appliance. The antimicrobial solution, in various aspects, may be safe to the user should, for example, any of the antimicrobial solution be ingested upon insertion of the dental appliance into the mouth following cleaning using the antimicrobial solution. In various aspects, the components of the antimicrobial solution fall under the umbrella approval of the FDA as "generally recognized as safe" ("GRAS"), meaning that all of the components are generally recognized by qualified experts as being generally safe under the Federal Food, Drug and Cosmetic Act.

As used in this disclosure, dental appliance includes a device worn by the user in the mouth. Dental appliance may include, for example, mouth guards, night guards (splints), orthodontic retainers, the mouth appliance associated with a cpap machine, and orthodontic braces. While the antimicrobial solution is generally shown and described herein in conjunction with a dental appliance, it should be recognized that the antimicrobial solution may be useful in the cleaning and disinfection of a variety of other surfaces or materials other than dental appliances, in various aspects.

As used in this disclosure, microorganism includes microscopic single or multi-cell organism, for example, bacteria, yeasts, molds, and viruses. Microorganism may include both Gram-positive and Gram-negative bacteria.

As used in this disclosure, plant-based antimicrobial extract includes any substance extracted from the seeds, pulp and/or fruit of a plant of the genus *Citrus* that has antimicrobial effects, including, for example, those obtained from the species consisting of bergamot or bitter orange (*Citrus aurantium*); grapefruit (*Citrus paradisi*); orange (*Citrius sinensis*); lemon (*Citrus limon*); lime (*Citrus aurantiifolia*); tangerine (*Citrus reticulata*); mandarin (*Citrus reticulata*); satsuma (*Citrus reticulata*); clementine (*Citrus reticulata*); citron (*Citrus medica*); pomelo (*Citrus grandis*); and mixtures thereof.

As used within this disclosure, allergy-inducing agent includes any chemical or other substance that, upon ingestion or topical contact, may cause the user to suffer an allergic reaction, such as inflammation, hives, skin irritation, itching, wheezing, anaphylactic swelling, nausea, diarrhea. Such agents may include, for example, sodium monopersulfate, sodium perborate, persulfates, and EDTA.

As used in this disclosure, safe and effective amount includes an amount of a plant-based antimicrobial extract or other antimicrobial compound or component sufficient to significantly induce a positive benefit, but low enough to avoid a serious side effect in the user—that is, to provide a reasonable benefit to risk ratio within the scope of sound medical judgment.

As used in this disclosure, chemically-derived malodor control agent includes chemically produced antimicrobial agents like 5-chloro-2-(2,4-dichlorophenoxy)-phenol (commonly known as Triclosan); phthalic acid and salts of phthalic acid, for example, magnesium mono-potassium phthalate, including but not limited to those disclosed in U.S. Pat. No. 4,994,262; chlorhexidine; alexidine; hexetidine; sanguinarine; benzalkonium chloride; salicylanilide;

domiphen bromide; cetylpyridinium chloride; tetradecylpyridinium chloride; N-tetradecyl-4-ethylpyridinium chloride; octenifine; delmopinol; octapinol; and other piperidine derivatives; nicin preparations; zinc/stannous ion agents; antibiotics such as augmentin, amoxicilline, tetracycline, doxycycline, minocycline, and metronidazole; and analogues and salts of the above; methyl salicyclate; and mixtures of all of the above.

The antimicrobial solution, as disclosed herein, may comprise: (i) deionized water quantum satis (Q.S); (ii) an effective amount of at least one plant-based antimicrobial extract compound; (iii) glycerin as a stabilizer and dilutant for the plant-based antimicrobial extract compound; (iv) glacial acetic acid as a cleaning agent; (v) sodium acetate as a buffer; (vi) macadamia oil derivative; (vii) a water soluble flavorant; and (viii) a colorant. The plant-based antimicrobial extract compound, glycerin, glacial acetic acid, sodium acetate, macadamia oil derivative, flavorant, and colorant may be generally regarded as benign at the concentrations of these components in various implementations of the antimicrobial solution.

An exemplary formulation of the antimicrobial solution is presented in Table 1. The components of the exemplary formulation of the antimicrobial solution as presented in Table 1 are listed by the component, the CAS (Chemical Abstracts Service) number of the component, the percentage of the component by weight in the exemplary formulation. Table 1 includes an exemplary range for each component in percentage by weight, as may be found in other exemplary formulations of the antimicrobial solution.

plary Table 1 may be possible without departing from the scope of this invention as defined in the Claims.

Deionized water QS constitutes at least 90% of the antimicrobial solution by weight in the exemplary formulation of Table 1. Accordingly, the exemplary antimicrobial solution of Table 1 may be considered as dilute.

Grapefruit seed Extract (GSE), which is the plant-based antimicrobial extract compound, is commercially available in liquid form as P-50 from Chemie Research and Manufacturing, PO BOX 181279, Casselberry, Fla. 32718. The GSE in the form of P-50 is exemplary, and other generally equivalent GSE from other suppliers may be used in other implementations of the antimicrobial solution. Note that GSE from some sources may contain benzyl alkonium chloride, and GSE that contains benzyl alkonium chloride may exhibit erratic performance as an antimicrobial agent. Therefore, it is important that the GSE not contain contaminants such as benzyl alkonium chloride as well as pesticide residue, herbicide residue, and the residue(s) of various other agricultural chemicals, in various implementations of the antimicrobial solution. P-50 has been found to be generally free of benzyl alkonium chloride and other contaminants.

P-50 is produced by Chemie Research and Manufacturing through the glycerin extraction of grapefruit pulp pellets obtained from the Florida Citrus Producers Cooperative. The grapefruit pulp pellets are a byproduct of various processing of grapefruits by the Florida Citrus Producers Cooperative. The extract is initially a dark brown in color,

TABLE 1

| COMPONENT | CAS # | % BY WEIGHT (EXEMPLARY FORMULATION) | RANGE (% BY WEIGHT) IN OTHER EXEMPLARY FORMULATIONS |
|---|---|---|---|
| DEIONIZED WATER | | Q.S. | |
| GRAPEFRUIT SEED EXTRACT (GSE) AS P-50 | 8496-38-8 | 2.0 | 0.5-2.5 |
| GLYCERIN 99% USP | 56-81-5 | 5.0 | 2.0-20.0 |
| GLACIAL ACETIC ACID | 64-19-7 | 0.25 | 0.2-1.0 |
| SODIUM ACETATE USP | 127-09-3 | 0.3 | 0.1-0.5 |
| *MACADAMIA* OIL DERIVATIVE AS FLORASOLVS PEG-16 *MACADAMIA* | 220459-99-4 | 0.5 | 0.25-1.0 |
| PEPPERMINT WATER SOLN. # 11837 FLAVOR | | 0.5 | 0.05-1.0 |
| FD&C BLUE #1 | 3844-45-9 | 0.1 | 0.05-0.2 |

The CAS number is a unique numerical identifier assigned to the component by the Chemical Abstracts Service that uniquely identifies the component. The Chemical Abstract Service has assigned a unique CAS number to each chemical substance described in the open scientific literature. The registry maintained by the Chemical Abstract Service includes chemical substances described from at least 1957 through the present and encompasses more than 81 million organic and inorganic substances and 64 million protein and DNA sequences. The registry is searchable by CAS number. Formulations of the antimicrobial solutions with components obtained from sources other than the specified sources, differing concentrations of the components, or components differing from that presented in exemand is diluted by the addition of glycerin to a lemon yellow in the final P-50 product. Thus, P-50 contains about 42% GSE. Accordingly, the 2.0% P-50 given in Table 1 translates to about 0.84% (by weight) GSE. The range of P-50 given in Table 1 translates to a range of about 0.21% GSE to about 1.05% GSE, by weight. The result of a spectral analysis of a sample of P-50 is given in Table 2. Physical properties of P-50 are given in Table 3 for a sample of P-50. The values in Table 2 and in Table 3 are provided for exemplary purposes only. It should be noted that P-50 is a product derived from agricultural sources, so that there may be some variation in the physical and chemical properties of P-50 in general correspondence with natural variations that may be inherent in the agricultural products from which P-50 is derived. GSE (as P-50) may be generally regarded as safe over the range of concentrations given in Table 1.

TABLE 2

RESULTS - ANALYSIS OF P-50 LIQUID

| COMPONENT | % BY WEIGHT |
|---|---|
| GRAPEFRUIT SEED EXTRACT (GSE) | 42.07% |
| ASCORBIC ACID (VITAMIN C) | 17.93% |
| GLYCERIN 99% USP | 38.38% |
| MOISTURE (MAX) | 1.62% |

TABLE 3

PROPERTIES OF R-50 LIQUID

| APPEARANCE | HEAVY VISCOUS LIQUID |
|---|---|
| COLOR | LEMON YELLOW TO GOLDEN BROWN |
| SPECIFIC GRAVITY | 1.19 |
| PH (D25° C.) | 2.26 |
| FLASH POINT | 292° F. |

GSE may contain a number of ingredients that exhibit antimicrobial activity. For example, the polyphenols found in GSE or in the seed or pulp extract derived from other fruits of genus Citrus may have antimicrobial activity. GSE, for example, may comprise at least some of the polyphenols quertcitin, quercetin glycoside, halperidin, campherol glycoside, apigenin, rutinoside, hepamothoxyflavone, and dihydrocampherol glycoside, which are stabilized by being converted to ammorium salts in the extract mixture. The flavonoids narigin, isocurametin, neohesperidin, hesperidin, poncirin, nebiletin, and tangeretin may be present in GSE or other seed or pulp extract of genus Citrus, and such flavonoids may provide antimicrobial activity.

Glycerine (1,2,3-trihydroxypropane—chemical formula $C_3H_8O_3$) acts as a stabilizer. Note that the P-50 includes glycerin. The glycerin listed in Table 1 is in addition to the glycerin included in the P-50.

Glacial acetic acid (ethanoic acid—chemical formula $CH_3COOH$) may act as a cleaning agent to remove microorganisms as well as foreign matter from the dental appliance. Foreign matter may include, for example, stains, debris, scale, and so forth. In undiluted form, acetic acid is referred to as glacial acetic. Acetic acid is considered a hydrophilic polar protic solvent. As such, acetic acid may act as a cleaning agent by dissolving polar compounds such as sugars and inorganic salts. Acetic acid may also act as a cleaning agent by dissolving non-polar compounds such as oils. Acetic acid mixes with both polar and non-polar solvents. Note that table vinegar may range from about 4% to about 8% acetic acid. A 1.0 M acetic acid solution, which is about the same concentration of vinegar, has a pH of 2.4. The range of acetic acid given in Table 1 is generally less than the concentration of acetic acid in table vinegar, so that antimicrobial solutions having acetic acid concentrations within this range may be generally regarded as safe.

Sodium acetate ($C_2H_3NaO_2$) is the sodium salt of acetic acid formed, for example, by the reaction of acetic acid with sodium hydroxide (NaOH), which is the reaction of a weak acid with a strong base. Sodium acetate is used to buffer the antimicrobial solution at a higher pH that may be less irritation to skin and mucosal membranes such at those found in the mouth. As the conjugate base of acetic acid, the addition of sodium acetate to the antimicrobial solution may act as a buffer to maintain the pH of the antimicrobial solution in a mildly acidic range of from a pH of about 6 to a pH of about 4. Sodium acetate is used in various food products. For example, sodium acetate may be used to impart a salt and vinegar flavor to potato chips. Accordingly, sodium acetate may be generally regarded as safe over the range of concentrations given in Table 1.

Macadamia oil derivative as Florasolvs PEG-16 Macadamia is a hydrophilic emollient (HLB from about 12 to about 14) derived from ethoxylated macadamia nut oil glycerides, and commercially available from Floratech Americas, 291 East El Prado Court, Chandler, Ariz. 85225. The macadamia oil derivative as Florasolvs PEG-16 Macadamia is exemplary, and generally equivalent macadamia oil derivatives available from other suppliers may be used in lieu of Florasolvs PEG-16 Macadamia, in other implementations of the antimicrobial solution. HLB refers to the Hydrophilic-Lipophilic Balance, which is a measure of the degree to which a surfactant is hydrophilic or lipophilic. The macadamia oil derivative as Florasolvs PEG-16 Macadamia is a wetting agent as the HLB of macadamia oil derivative as Florasolvs PEG-16 Macadamia falls within the range of 11 to 14. The macadamia oil derivative as Florasolvs PEG-16 Macadamia is a surface-active agent (surfactant) that enhances wetting of the dental apparatus by the antimicrobial solution, and, thus, may enhance cleaning performance of the antimicrobial solution. The surface-activity of the macadamia oil derivative as Florasolvs PEG-16 Macadamia may assist the antimicrobial solution in penetrating pores within the dental appliance that may harbor microorganisms within.

Florasolvs PEG-16 Macadamia is not classified as hazardous or dangerous according to (EC) 1272/2008, 67/548/EEC, or 1999/45/EC. Ingestion of a single dose is unlikely to cause harm. This material is exempt from the Toxic Substances Control Act. Accordingly, macadamia oil derivative as Florasolvs PEG-16 Macadamia may be generally regarded as safe over the range of concentrations given in Table 1.

Peppermint water solution #11837 is commercially available from Berje Inc. 700 Blair Road Carteret, N.J. USA 07008. Peppermint water solution #11837 is exemplary, and generally equivalent flavorant available from other suppliers may be used in lieu of peppermint water solution #11837 in other implementations of the antimicrobial solution. Peppermint water solution #11837 is a water-soluble peppermint flavorant used to impart a peppermint flavor to the antimicrobial solution. The flavorant, if any, included in the antimicrobial solution may, at least in part, deodorize the dental appliance. Dental appliances tend to collect foreign matter over time, which may lend a foul odor to the dental appliance. The flavorant may mask this odor, and make the dental appliance more palatable to the user. Other flavorants having that impart other flavors may be used in the antimicrobial solution, in other implementations. The flavorant may be omitted from the antimicrobial solution, in yet other implementations. Peppermint water solution #11837 may include plant extracts from the peppermint plant, and may be commonly ingested. Accordingly, peppermint water solution #11837 may be generally regarded as safe over the range of concentrations given in Table 1.

FD&C Blue #1 ($C_{37}H_{34}N_2O_9S_3Na_2$) is commercially available from Sciencelab.com Inc. 14025 Smith Rd. Houston Tex. 77396. FD&C Blue #1 is exemplary, and generally equivalent colorants available from other suppliers may be used in lieu of FD&C Blue #1 in other implementations of the antimicrobial solution. FD&C Blue #1 is an FDA approved colorant that is water soluble and that is used to give a light green color to the antimicrobial solution. Inclusion of a colorant, such as FD&C Blue #1, may enhance the visual presentation of the antimicrobial solution, for example, the uniformity of the antimicrobial solution's appearance. Other colorant(s) having other colors may be used in the antimicrobial solution, in other implementations. The colorant may be omitted from the antimicrobial solution, in yet other implementations. FD&C Blue #1 may be generally regarded as safe over the range of concentrations given in Table 1.

The GSE or other plant-based antimicrobial extract agent in the antimicrobial solution may act to reduce the incidence of or eradicate microorganisms from the dental appliance, while the acetic acid acts as a cleaning agent to remove stains and odors from the surfaces of the dental appliance. The macadamia oil derivative may act as surfactant that enhances wetting and, hence, penetration of the antimicrobial solution into pores of the dental appliance to contact the pores and microorganisms within the pores with the antimicrobial solution. Accordingly, the GSE, the acetic acid, and the macadamia oil derivative may act synergistically with one another. The acetic acid acting as a cleaning agent acting to remove foreign matter from the dental appliance so that the GSE may better access to the microorganisms obscured by the foreign matter to eradicate the microorganisms from the dental appliance. The acetic acid may remove microorganisms including those killed by the GSE from the dental appliance. By enhancing wetting, the macadamia oil derivative may facilitate cleaning within pores by the acetic acid, and the macadamia oil derivative may facilitate eradication of microorganisms within pores by the GSE.

The antimicrobial solution, in various formulations, does not include various components as may be found in other antimicrobial solutions that may cause irritation, allergic reactions, or other deleterious effects to the user. The antimicrobial solution in the exemplary formulation of Table 1 does not include or any multivalent metal cation such as $Al^{+++}$, $Cu^{++}$, or $Zn^{++}$. Metal cations such as $Al^{+++}$, $Cu^{++}$ or $Zn^{++}$ have been included in other antimicrobial solutions to increase the effectiveness of antimicrobial properties of such other antimicrobial solutions and to fight oral malodor. The antimicrobial solution in the exemplary formulation of Table 1 does not include non-alkali metal cations such as $Ag^+$. EDTA may be included in such other antimicrobial solutions as a chelating agent to assist in reducing the amount of absorption of multivalent metal cations into the body. The antimicrobial solution disclosed herein foregoes such multivalent metal cations.

The antimicrobial solution, in various formulations, does not include anti-calculus agents like phosphate, pyrophosphate, polyphosphate, phosphonate, polyphosphonate, and aluminum compounds are common ingredients found in dental care products. Such anti-calculus agents may cause skin irritation or allergy in the user.

The antimicrobial solution, in various formulations, does not include anti-plaque agents. Examples of anti-plaque agents may include xylitol, ammonium fluoride, chlorothymol, stannous fluoride, and urea peroxide.

The antimicrobial solution, in various formulations, does not include fluoride. The antimicrobial solution of the exemplary formulation of Table 1 does not include fluoride, alcohol, alkanediols, Cholorheidine Gluconate, tocopheryl acetate, or hydrogen peroxide.

The antimicrobial solution, in various formulations, does not include a desensitizing agent. Examples of desensitizing agents, which may act as anti-pain agents for topical treatment of sore gums and inner cheeks, include strontium chloride, potassium nitrate, natural herbs like gall nut, asarum, cubebin, Galasega, and other non-steroidal anti-inflammatory agents.

The antimicrobial solution, in various formulations, does not include a chemically-derived malodor control agent for fighting microorganisms in the user's mouth that cause, e.g., halitosis ("bad breath"). Examples of chemically derived moral malodor control agents may include triclosan, phthalic acid and its salts, magnesium mono-potassium phthalate, chlorhexidine, sanguinarine, benzalkonium chloride, salicylanilide, domiphen bromide, and tetradecylpyridinium chloride ("TPC").

The antimicrobial solution, in various formulations, does not include parabens or sodium lauryl sulfate ("SLS").

The antimicrobial solution, in various formulations, does not include an H-2 antagonist, which is a compound that block H-2 receptors and that may lead to skin irritation, redness, swelling, and anaphylactic side effects.

In preparing the antimicrobial solution, for example, the exemplary formulation of Table 1, the glycerin and glacial acetic acid may be added consecutively to the deionized water in a tank and mixed. Next, the GSE may be added to the mixture and thoroughly mixed. Then, the sodium acetate may be added to the mixture. Finally, the Peppermint water solution #11837, the Florasolvs PEG-16 Macadamia, and the FD&C Blue #1 may be added to the mixture, in no particular order. The mixture may be thoroughly mixed in the tank by means of an impeller mixer at room temperature. The amount of colorant added may be adjusted to attain a desired color of the antimicrobial solution. The resulting antimicrobial solution may be stored at room temperature until use.

The formulation of antimicrobial solution as given in Table 1 was tested in a disk diffusion assay. As set forth in Table 1, the formulation of antimicrobial solution so tested included 2% GSE (as P-50), 5% glycerin, 0.04165M sodium acetate, and 0.04165M acetic acid. Tests were performed in duplicate, and distilled water was used as a negative control. Sterile paper disks soaked with 20 μL of antimicrobial solution were placed on agar plates spread with each species of bacteria. The plates were incubated overnight at 35° C., and diameters of clear zones of growth inhibition were measured in millimeters. Averages of the results for the duplicate tests are given in FIG. 8.

Figure 8:
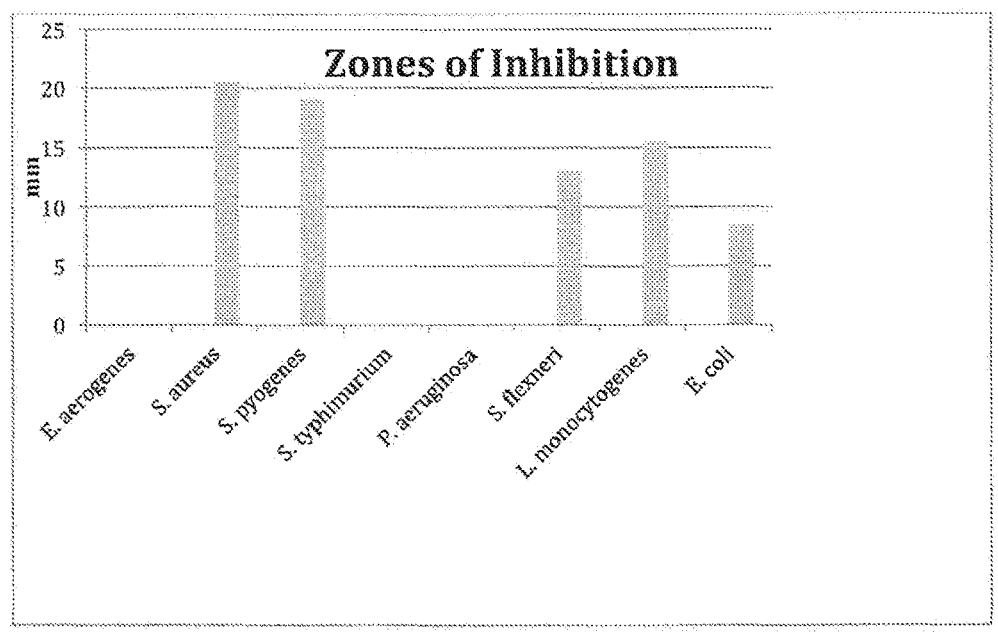
FIG. 8 illustrates by bar chart results of a test of the exemplary antimicrobial solution of Table 1 against various microorganisms.

As illustrated in FIG. 8, the test included the microorganisms:
- *E. coli* (Gram-negative) facultative anaerobe found in the gut. While most are harmless, some variants may cause food poisoning.
- *L. monocytogenes* (Gram-positive) is a facultative anaerobe that causes listerosis. May be a virulent food borne pathogen.
- *S. flexneri* (Gram-negative) causes diarrhea in humans May be resistant to antibiotics
- *S. Pyogenes* (Gram-positive)—hemolysis—mild superficial skin infections to life-threatening systemic diseases usually beginning in the throat (pharyngitis) or skin (impetigo)
- *S aureus* (Gram-positive)—*S. aureus* can cause a range of illnesses, from minor skin infections such as pimples, impetigo, boils (furundes), cellulitis folliculitis, carbuncies, scalded skin syndrome, and abscesses to serious conditions such as pneumonia, meningitis, osteomyelitis, endocarditis, sepsis, toxic shock syndrome, and bacteremia. Its incidence ranges from skin, soft tissue, respiratory, bone, joint, endovascular to wound infections. It is still one of the five most common causes of nosocomial infections and is often the cause of postsurgical wound infections.

As illustrated in FIG. 8, the antimicrobial solution is effective against the range of microorganisms in the test. The microorganisms in the test include both Gram-positive and Gram-negative bacteria. The microorganisms in the test encompass both common generally benign bacteria and pathogens.

Various exemplary formulations of the antimicrobial solution, which are given in Table 4, were tested by disk diffusion assay for effectiveness as an antimicrobial agent against a suite of microorganisms. Distilled MilliQ water was used as a negative control. All of the formulations of Table 4 contained 2% GSE, 0.04165M Na Acetate, 0.04165M Acetic Acid, and 5% glycerin. The variations in the formulations of Table 4 were in the flavorant and colorant. The formulations of Table 4 include various combinations of no flavorant, peppermint flavorant, or spearmint flavorant and either blue colorant or no colorant.

In conducting the tests of the Table 4 formulations, sterile paper disks soaked with 20 µL of solution were placed on agar plates spread with each species of bacteria. The plates were incubated overnight at 35° C., and diameters of zones of growth inhibition were measured in millimeters. Each assay was performed in duplicate. Diameters of zones of growth inhibition were measured, and averages were found for duplicate assays.

TABLE 4

| FORMULATION | FLAVORANT | COLORANT |
| --- | --- | --- |
| MAC1 5-21-14 | NONE | BLUE |
| MAC1 PEPPERMINT | PEPPERMINT | BLUE |
| MAC1 SPEARMINT | SPEARMINT | BLUE |
| MAC1 4-26-14 | NONE | NONE |

Figure 10:
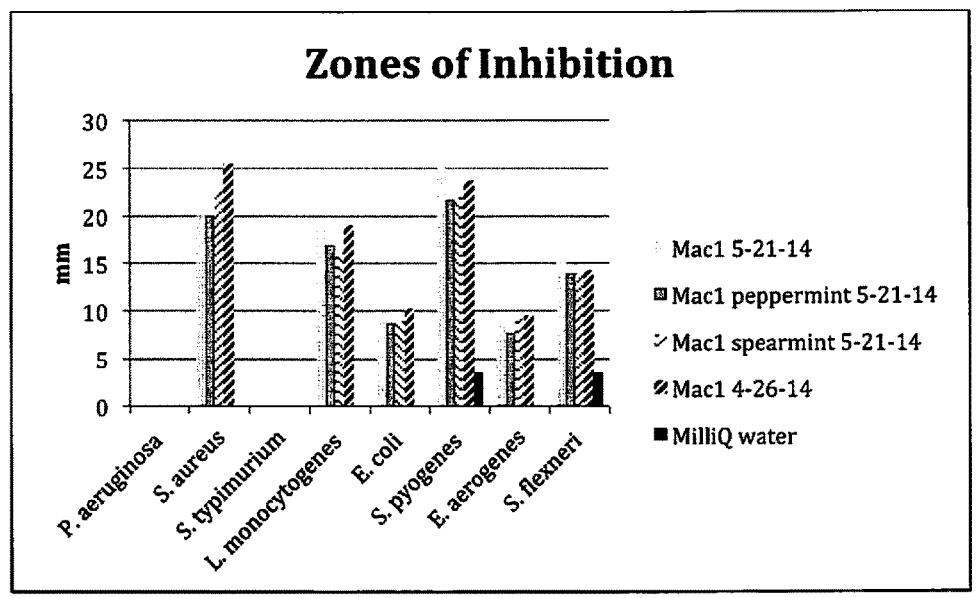

In the tests of the Table 4 formulations, the largest growth inhibition was observed for *S. aureus* and *S. pyogenes* and some inhibited growth was observed for *S. flexneri, L. monocytogenes, E. coli* and *E. aerogenes*. Results are presented graphically in FIG. 10, which plots the diameters of zones of growth inhibition in mm for each microorganism tested. As indicated in FIG. 10, the presence or absence of colorant in the antimicrobial solution did not appear to materially alter the effectiveness of the antimicrobial solution against the microorganisms tested. Similarly, neither the presence or absence of the flavorant nor the type of flavorant (peppermint or spearmint) appeared to materially alter the effectiveness of the antimicrobial solution against the microorganisms tested, as indicated in FIG. 10.

The antimicrobial solution may be provided to the end user in the form of a liquid cleansing rinse or soaking solution. An exemplary dental appliance 10, which is in the form of a mouth guard, is illustrated in FIG. 1. Meant to be worn by a user around the upper line of teeth, this implementation of dental appliance 10 comprises an exterior u-shaped body 12 containing a thermally-moldable plastic material 14 in which the user's teeth have been inset to form an imprint 16 therein for each tooth, as illustrated. When the dental appliance 10 is placed into the user's mouth and along the upper gum line, the user's teeth enter these imprint channels 16 so that the mouth guard may fit around the teeth and gum line to protect the teeth.

Figure 2:
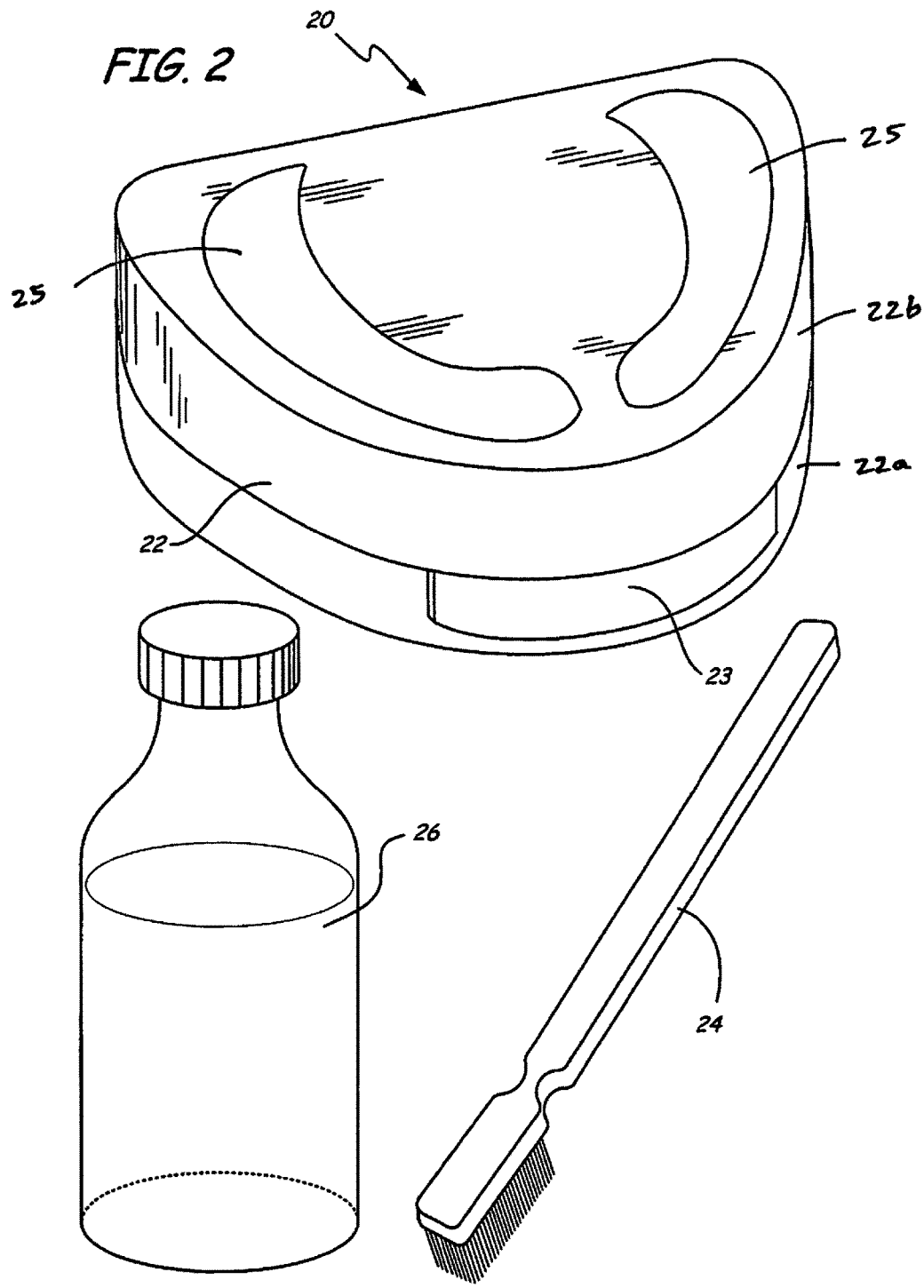
FIG. 2 illustrates by a perspective view an exemplary antimicrobial dental appliance cleaning kit.

As shown in FIG. 2, an exemplary cleaning kit 20 includes a protective case 22 for holding the dental appliance such as the dental appliance 10, a soft bristled brush 24, and a bottle 26 containing a formulation of the antimicrobial solution as disclosed herein. The case 22 may be made from any appropriate cleanable material including plastic, ceramic, glass, or metal. The case 22 contains a housing 22a and lid 22b, which is hinged to the housing along its one edge (not shown) and releasably secured to the housing along another edge by means of clasp 23, in this implementation. Alternatively, in other implementations, the lid housing 22b may contain a lip extending around its perimeter, which cooperates with a rabbit groove extending around housing 22a so that the lid may be snap fitted onto the housing. The lid may feature optional vents 25 for allowing air to circulate into the case containing the dental appliance to remove moisture that may allow microorganisms to grow within case 22.

Figure 3:
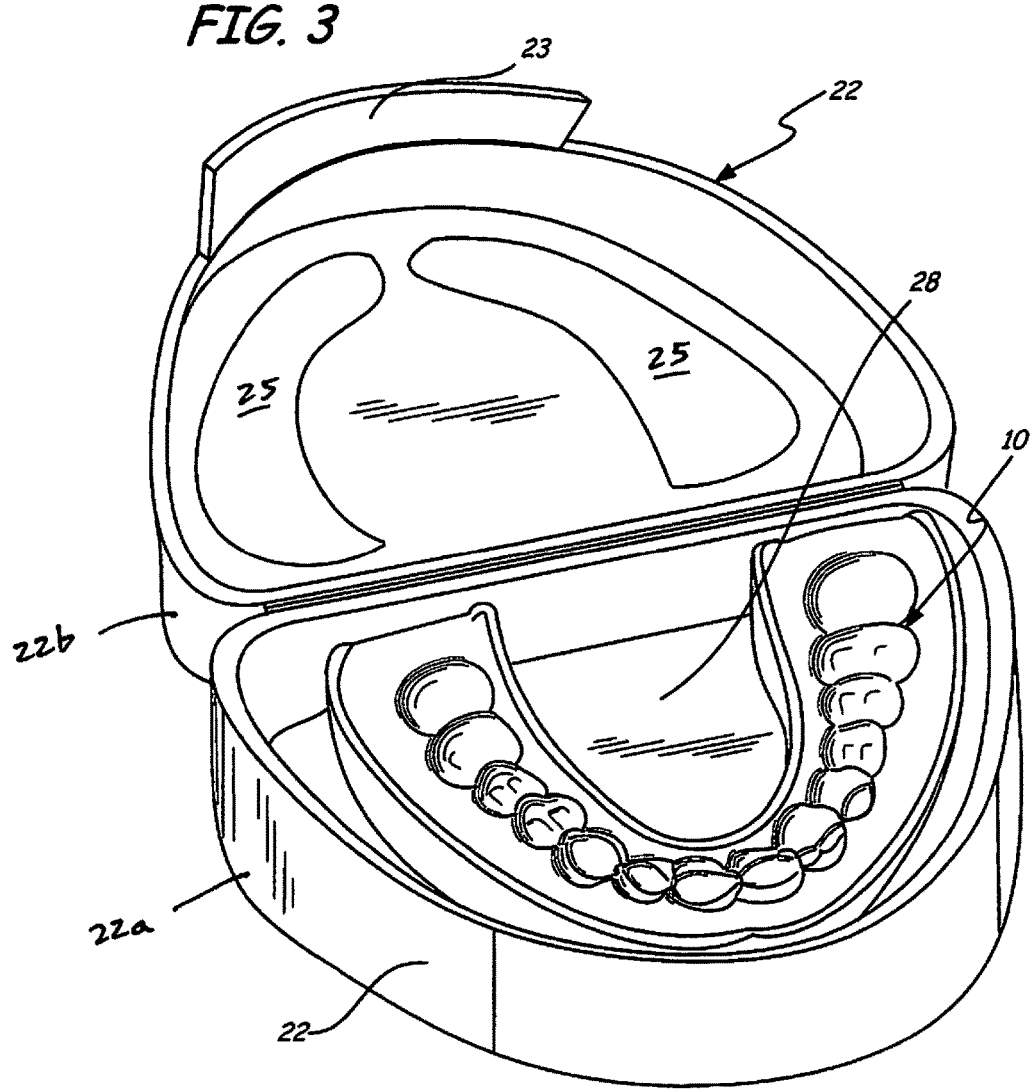
FIG. 3 illustrates by a perspective view portions of the exemplary cleaning kit of FIG. 2 opened to show the exemplary dental appliance of FIG. 1 contained therein.

As shown in FIG. 3, case 22 may be sized, so that its interior volume 28 not only accommodates the dental appliance 10, but also secures dental appliance 10 in place without allowing dental appliance 10 to slide around, which may cause damage to dental appliance 10.

For daily cleaning, for example, the dental appliance 10 may have a portion of the antimicrobial solution poured onto it for less than one minute, followed by light brushing using brush 24 to enhance contact by the antimicrobial solution with microorganisms existing on the surfaces 14 of the dental appliance 10 and inside tooth imprint channels 16 therein. The dental appliance 10 may then be rinsed with cool water and stored in case 22.

For weekly cleaning, for example, the dental appliance 10 may be soaked in the antimicrobial solution, which has been poured into the case 22 or other suitable container holding the dental appliance 10. The dental appliance 10 may be soaked in this antimicrobial solution for a time period ranging from one minute to 24 hours. The dental appliance 10 may be soaked in this antimicrobial solution for a time period ranging from 10 minutes to 12 hours. The dental appliance 10 may be soaked in this antimicrobial solution for a time period ranging from 15-30 minutes. Following soaking, the dental appliance 10 may be removed from the container, brushed with brush 24, rinsed with cool water, and stored in case 22.

In various other implementations, the dental appliance 10 may be soaked in the cleaning composition for 2-24 hours or for a time period ranging 3-12 hours, depending upon the amount of microorganisms collected by the dental appliance 10.

Figure 4:
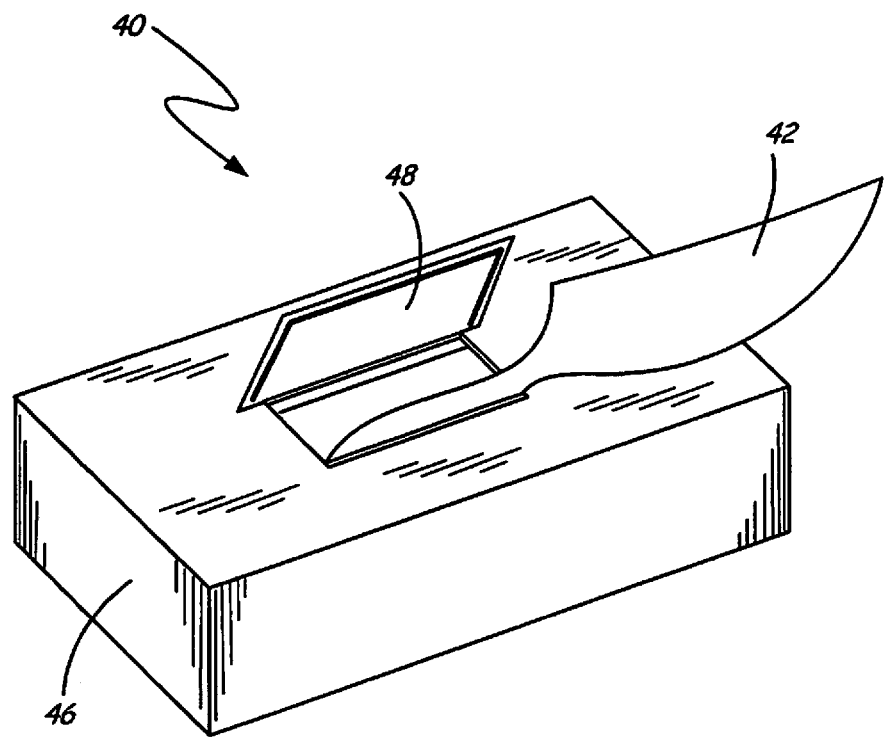
FIG. 4 illustrates by a perspective view an exemplary package of towelettes.

In an alternate mini-wipes embodiment 40 shown in FIG. 4, the antimicrobial solution may be incorporated into a towelette 42, which may be contained within an airtight package 44 until use. Such towelettes 42 may be made from paper, cloth, or other fiber products, and the towelettes 42 may be provided as discrete sheets or tear away panels. Each sheet or panel may be impregnated with the antimicrobial solution, to ensure full coverage by the solution throughout the sheet. The towelette 42 should be robust enough to not disintegrate upon use; but may be designed to biodegrade over time after its use, in various implementations. For example, the towelettes 42 may comprise a spun-lace, non-woven fabric made from, e.g., 100% cotton, 50% viscose, or 50% polyester, in various implementations.

The towelette panel size may be approximately 2.75 inches×4 inches (7.5 cm×10 cm), in various implementations. The towelettes 42 may be packaged in a moisture-impermeable container 46 made from thin, flexible material, such as plastic, vinyl, or foil. Unless only a single towelette is contained in such a package 46 (i.e., a single-use wipe), the package may contain a peel-away flap 48 for dispensing one towelette sheet at a time to the user with a re-seal capability for securing the flap 48 to the package to keep the unused towelettes moist. The package 46, in this implementation, has a small hook and loop fastener strip on its back to enable the user to attach the towelette package 46 to a cooperating hook and loop fastener strip mounted to a side of the dental appliance case 22, so that towelettes containing the antimicrobial solution of this invention may be available with case 22 for cleaning the dental appliance 10.

Figure 5:
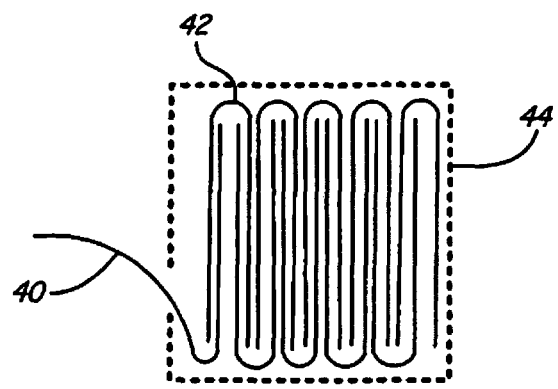
FIG. 5 illustrates by a schematic view an exemplary implementation of the packaged towelettes of FIG. 4.

The towelettes 42 rectangular or square panels may be folded in upon themselves in bipartite panels overlapping between individual towelettes in an "accordion" arrangement, as shown in FIG. 5. In this manner, pulling the leading edge 40 of a towelette 42 to take possession of it will cause the next towelette 42 to be pulled forward to the standby position, in this implementation. A block of, e.g., 15 sheets stacked in this accordion arrangement may be dropped into the package and sealed to maintain the moisture of the antimicrobial cleaning solution, in various implementations.

Figure 6:
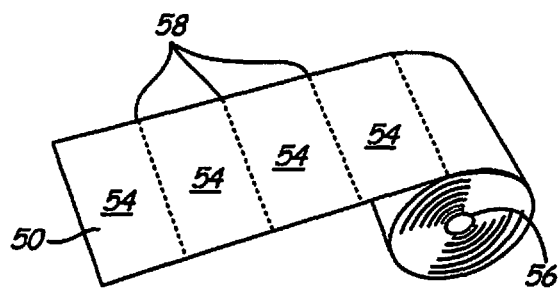
FIG. 6 illustrates by a schematic view another exemplary implementation of the packaged towelettes of FIG. 4.
Figure 7:
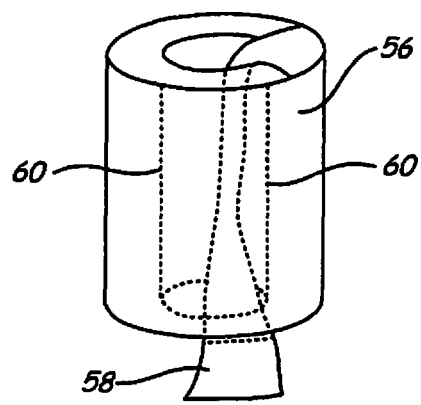
FIG. 7 illustrates by a schematic view yet another implementation of the packaged wet wipes towelettes of FIG. 4.

Instead of individual towelettes, the towelette may also constitute one long ribbon 50 on a roll with a multitude of serrated cuts 52 to form individual panels 54, as illustrated in FIG. 6. The towelette roll may be wound into a roll 56, so that pulling the first panel will not only allow it to be separated from the roll along the serration line, but also pull the next panel into the standby position. In still another implementation, the towelette ribbon 50 may be internally wound so that the leading edge 58 is on the inside of the roll, instead of the outside, as illustrated in FIG. 7. Such an arrangement, with internal winding 60 of the ribbon roll, may provide more resistance to the towelettes as they are pulled and separated from the roll, and may contain the antimicrobial solution impregnated within the towelettes more completely in order to reduce evaporation.

Figure 9A:
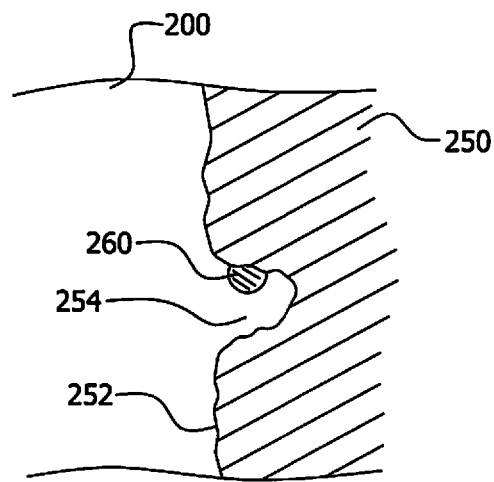
FIG. 9A illustrates by side cut-away view an implementation of the antimicrobial solution in use with portions of an exemplary dental appliance.

In use, the antimicrobial solution 200 may contact a surface 252 of dental appliance 250, as illustrated in FIG. 9A, by immersion of dental appliance 250 into antimicrobial solution, by being sprayed upon dental appliance 250, or being poured upon dental appliance 250. Microorganisms 260, which adhere to surface 252, may be growing on surface 252 including within pore 254 formed in dental appliance 250, and the antibacterial solution 200 may penetrate pore 254 to eradicate microorganisms 260 within pore 254. The surfactant properties of macadamia oil derivative and the solvent and hydrophylic polar protic properties of acetic acid may enhance the penetration of antimicrobial solution 200 into pore 254, and, hence, the eradication of microorganisms 260 including within pore 254. Exemplary pore 254 may be formed in either a metal portion or a plastic portion of dental appliance 250, in various implementations.

Figure 9B:
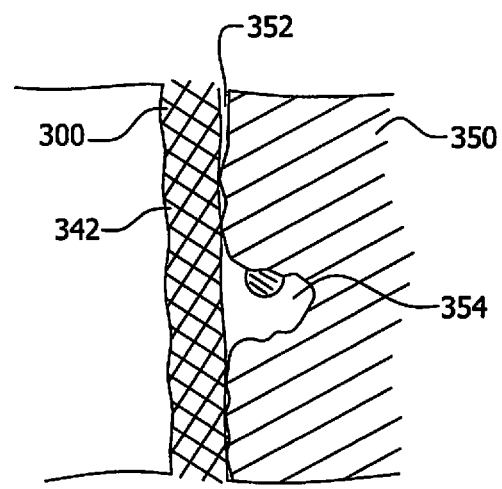
FIG. 9B illustrates by side cut-away view an implementation of a towelette in combination with an exemplary antimicrobial solution in use with portions of an exemplary dental appliance; and, FIG. 10 illustrates by bar chart the results of tests of various exemplary formulations of the antimicrobial solution as given in Table 4 against various microorganisms.

In use, the antimicrobial solution 300 be included within towelette 342, as illustrated in FIG. 9B. Towelette 342 may be biased against surface 352 of dental appliance 350 to apply the antimicrobial solution 300 to surface 350 in order to eradicate microorganisms on surface 352 and to wipe foreign matter from surface 352. Antimicrobial solution 300 may penetrate from towelette 342 into pore 354 to eradicate microorganisms within pore 354, in this implementation.

The foregoing discussion along with the Figures discloses and describes various exemplary implementations. These implementations are not meant to limit the scope of coverage, but, instead, to assist in understanding the context of the language used in this specification and in the claims. Upon study of this disclosure and the exemplary implementations herein, one of ordinary skill in the art may readily recognize that various changes, modifications and variations may be made thereto without departing from the spirit and scope of the inventions as defined in the following claims.

The invention claimed is:

1. An antimicrobial solution consisting of:
deionized water QS;
one or more materials extracted from grapefruit pulp and having antimicrobial properties, the one or more materials at a concentration in said antimicrobial solution effective to eradicate microorganisms;
glycerine;
acetic acid at a concentration in said antimicrobial solution between about 0.2% by weight and about 1.0% by weight;
sodium acetate as a buffer at a quantity sufficient to maintain said antimicrobial solution at a pH of from about 4 to about 6;
ethoxylated macadamia nut oil glycerides;
a colorant that is water soluble; and
a flavorant that is water soluble.

2. The antimicrobial solution of claim 1, the one or more materials comprise a polyphenol.

3. The antimicrobial solution of claim 1, the one or more materials comprise ascorbic acid.

4. The antimicrobial solution of claim 1 and a dental appliance having microorganisms resident upon the surface, wherein the antimicrobial solution is in contact with the microorganisms.

5. The antimicrobial solution and dental appliance of claim 4 wherein the dental appliance is a mouth guard.

6. The antimicrobial solution of claim 1 and a solid material in contact with said antimicrobial solution for disinfection by said antimicrobial solution.

7. The antimicrobial solution of claim 1 and a towelette that incorporates the antimicrobial solution.

8. An antimicrobial solution consisting of:
deionized water QS;
grapefruit seed extract (GSE) at a concentration in said antimicrobial solution between about 0.21% by weight and about 1.05% by weight;
glycerine;
acetic acid at a concentration in said antimicrobial solution between about 0.2% by weight and about 1.0% by weight;
sodium acetate as a buffer at a quantity sufficient to maintain said antimicrobial solution at a pH of from about 4 to about 6;
ethoxylated macadamia nut oil glycerides;
a colorant that is water soluble; and
a flavorant that is water soluble.

9. The antimicrobial solution of claim 8 and a solid material wherein the antimicrobial solution is in contact with the solid material thereby disinfecting the solid material.

10. The antimicrobial solution and solid material of claim 9 wherein the solid material is a mouth guard.

11. The antimicrobial solution of claim 8 and a towelette that incorporates the antimicrobial solution.

12. The antimicrobial solution of claim 8, wherein the grapefruit seed extract (GSE) comprises a material selected from a group consisting of a polyphenol and ascorbic acid.

* * * * *